United States Patent
Baldwin

(10) Patent No.: US 11,801,131 B2
(45) Date of Patent: Oct. 31, 2023

(54) ELLIPTICAL HEART VALVE PROSTHESES, DELIVERY SYSTEMS, AND METHODS OF USE

(71) Applicant: Medtronic Vascular, Inc., Santa Rosa, CA (US)

(72) Inventor: Matthew Baldwin, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 176 days.

(21) Appl. No.: 16/724,136

(22) Filed: Dec. 20, 2019

(65) Prior Publication Data

US 2021/0186694 A1  Jun. 24, 2021

(51) Int. Cl.
*A61F 2/24* (2006.01)

(52) U.S. Cl.
CPC .......... *A61F 2/2418* (2013.01); *A61F 2/2412* (2013.01); *A61F 2/2433* (2013.01); *A61F 2230/0008* (2013.01); *A61F 2250/0018* (2013.01); *A61F 2250/0029* (2013.01); *A61F 2250/0036* (2013.01); *A61F 2250/0037* (2013.01); *A61F 2250/0098* (2013.01)

(58) Field of Classification Search
CPC .................. A61F 2/2433; A61F 2/2418; A61F 2230/0054; A61F 2250/0036; A61F 2250/0018; A61F 2230/0008; A61F 2/24–2424; A61F 2/2475
See application file for complete search history.

(56) References Cited

U.S. PATENT DOCUMENTS

| | | | |
|---|---|---|---|
| 5,415,667 | A | 5/1995 | Frater |
| 6,562,069 | B2 | 5/2003 | Cai et al. |
| 6,890,350 | B1 | 5/2005 | Walak |
| 7,101,396 | B2 | 9/2006 | Artof et al. |
| 7,455,689 | B2 | 11/2008 | Johnson |
| 2003/0069635 | A1 | 4/2003 | Cartledge et al. |
| 2004/0168298 | A1* | 9/2004 | Dolan ............... A61F 2/91 219/121.72 |
| 2005/0075584 | A1* | 4/2005 | Cali ............... A61F 2/2418 623/2.11 |
| 2005/0137682 | A1 | 6/2005 | Justino |
| 2005/0228472 | A1* | 10/2005 | Case ............... A61F 2/2475 623/1.1 |
| 2005/0228486 | A1 | 10/2005 | Case et al. |

(Continued)

FOREIGN PATENT DOCUMENTS

| | | | | |
|---|---|---|---|---|
| CN | 1223562 A | * | 7/1999 | ........... A61F 2/2412 |
| DE | 102012107175 A1 | * | 12/2013 | ....... A61B 17/12036 |

OTHER PUBLICATIONS

International Search Report and Written Opinion in PCT/US2020/062657, dated Apr. 1, 2021.

*Primary Examiner* — Rebecca S Preston
(74) *Attorney, Agent, or Firm* — Medler Ferro Woodhouse & Mills PLLC

(57) ABSTRACT

A heart valve prosthesis includes a frame and a prosthetic disposed within a lumen of the frame. The frame includes a plurality of struts and crowns and has a radially collapsed state and a radially expanded state. A stiffness of the plurality of struts is varied by varying the width of at least one strut of the plurality of struts such that when the frame is in the radially expanded state, the frame has a substantially elliptical shape.

18 Claims, 13 Drawing Sheets

(56) References Cited

U.S. PATENT DOCUMENTS

| | | |
|---|---|---|
| 2008/0183273 A1* | 7/2008 | Mesana ................ A61F 2/2433 623/1.11 |
| 2009/0054973 A1 | 2/2009 | Johnson |
| 2010/0286768 A1 | 11/2010 | Alkhatib |
| 2011/0040366 A1 | 2/2011 | Goetz et al. |
| 2012/0239143 A1* | 9/2012 | Rankin ................ A61F 2/2418 623/2.37 |
| 2012/0277734 A1 | 11/2012 | Goetz et al. |
| 2013/0023980 A1 | 1/2013 | Drasler |
| 2013/0096664 A1 | 4/2013 | Goetz et al. |
| 2013/0096670 A1 | 4/2013 | Goetz et al. |
| 2013/0103131 A1 | 4/2013 | Goetz et al. |
| 2013/0245752 A1 | 9/2013 | Goetz et al. |
| 2013/0325101 A1 | 12/2013 | Goetz et al. |
| 2013/0338755 A1 | 12/2013 | Goetz et al. |
| 2014/0330368 A1 | 11/2014 | Gloss et al. |
| 2015/0112430 A1 | 4/2015 | Creaven et al. |
| 2015/0209140 A1* | 7/2015 | Bell ..................... A61F 2/2418 623/2.18 |
| 2016/0089236 A1 | 3/2016 | Kovalsky et al. |
| 2017/0042673 A1* | 2/2017 | Vietmeier ............ A61F 2/2418 |

* cited by examiner

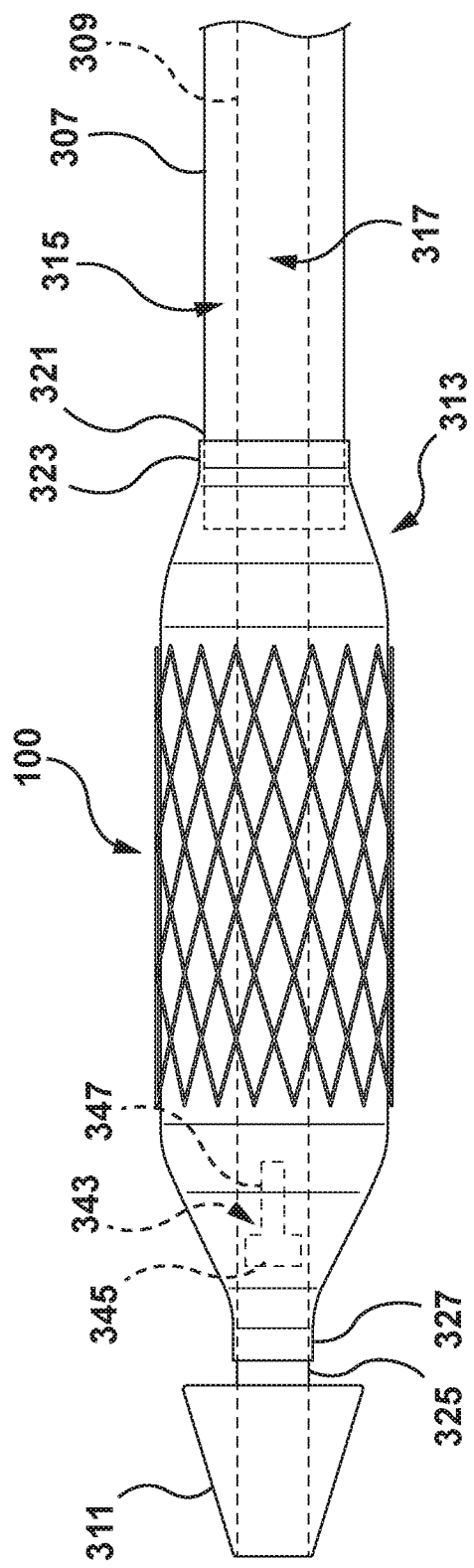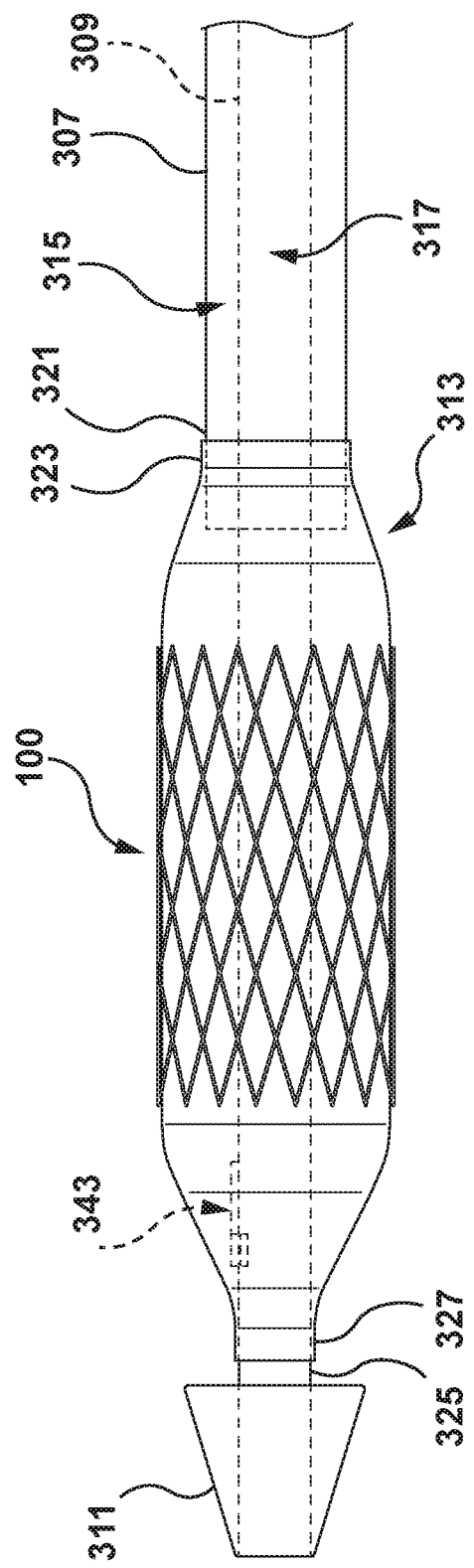

ELLIPTICAL HEART VALVE PROSTHESES, DELIVERY SYSTEMS, AND METHODS OF USE

FIELD OF THE INVENTION

The present invention relates to elliptical heart valve prostheses, and systems and methods for delivering and deploying elliptical heart valve prostheses. More particularly, the present invention relates to an elliptical shaped heart valve prosthesis wherein the width of the struts of the heart valve prosthesis are varied to form the elliptical shape.

BACKGROUND OF THE INVENTION

The human heart is a four chambered, muscular organ that provides blood circulation through the body during a cardiac cycle. The four main chambers include the right atria and the right ventricle which supplies the pulmonary circulation, and the left atria and the left ventricle which supplies oxygenated blood received from the lungs to the remaining body. To ensure that blood flows in one direction through the heart, atrioventricular valves (tricuspid and mitral valves) are present between the junctions of the atria and the ventricles, and semi-lunar valves (pulmonary valve and aortic valve) govern the exits of the ventricles leading to the lungs and the rest of the body. These valves contain leaflets or cusps that open and shut in response to blood pressure changes caused by the contraction and relaxation of the heart chambers. The leaflets move apart from each other to open and allow blood to flow downstream of the valve, and coapt to close and prevent backflow or regurgitation in an upstream manner.

Diseases associated with heart valves, such as those caused by damage or a defect, can include stenosis and valvular insufficiency or regurgitation. For example, valvular stenosis causes the valve to become narrowed and hardened which can prevent blood flow to a downstream heart chamber from occurring at the proper flow rate and may cause the heart to work harder to pump the blood through the diseased valve. Valvular insufficiency or regurgitation occurs when the valve does not close completely, allowing blood to flow backwards, thereby causing the heart to be less efficient. A diseased or damaged valve, which can be congenital, age-related, drug-induced, or in some instances caused by infection, can result in an enlarged, thickened heart that loses elasticity and efficiency. Some symptoms of heart valve diseases can include weakness, shortness of breath, dizziness, fainting, palpitations, anemia and edema, and blood clots which can increase the likelihood of stroke or pulmonary embolism. Symptoms can often be severe enough to be debilitating and/or life threatening.

In recent years, heart valve prostheses for percutaneous transcatheter delivery and implantation have been developed. The heart valve prosthesis is radially compressed or collapsed for delivery in a catheter and then advanced, for example through an opening in the femoral artery, through the aorta, where the valve prosthesis is then deployed in the annulus of a native heart valve. Valve prostheses are generally formed by attaching a prosthetic valve to a frame or stent made of a wire or a network of wires. The valve prosthesis may be deployed by radially expanding it once positioned at the desired deployment site.

Most heart valve prostheses are of a circular cross-section. However, a large population of patients have bicuspid valves that are non-circular, or elliptical in shape. Round or circular heart valve prostheses deployed within a noncircular or elliptical native anatomy have an increased potential for para-valvular leakage (PVL), a serious post-implantation condition. Accordingly, there is a need for improved, elliptical shaped heart valve prostheses, and systems and methods for deploying elliptical shaped heart valve prostheses.

BRIEF SUMMARY OF THE INVENTION

Embodiments hereof relate to a heart valve prosthesis include a frame including a lumen, and a prosthetic valve disposed within the lumen of the frame. The frame further includes a plurality of struts forming a plurality of crowns, an inflow end, and an outflow end opposite the inflow end. The frame further includes a radially collapsed state and a radially expanded state. A stiffness of the plurality of struts is varied such that when the frame is in the radially expanded state, the frame is substantially elliptically shaped in cross-section.

In any of the embodiments, the stiffness of the plurality of struts may be varied by varying a width of at least one strut of the plurality of struts such that when the frame is in the radially expanded state, at least one strut with a greatest width of the plurality of struts is disposed adjacent a major axis of the frame, and at least one strut with a smallest width of the plurality of struts is disposed adjacent a minor axis of the frame.

In any of the embodiments, the width of each strut of the plurality of struts of the frame may be selected from a group consisting of a first strut width, a second strut width, a third strut width, a fourth strut width, and a fifth strut width.

In any of the embodiments, at least one of the inflow end or the outflow end of the frame comprises eighteen crowns formed by struts of the plurality of struts. In any of the embodiments, the plurality of struts forming the eighteen crowns each have a width selected from a group consisting of a first width, a second width, a third width, a fourth width, and a fifth width. In any of the embodiments, each of the eighteen crowns are formed by two struts such that the plurality of struts consists of thirty-six struts including four struts of the first width, eight struts of the second width, eight struts of the third width, eight struts of the fourth width, an eight struts of the fifth width, wherein the second width is greater than the first width, the third width is greater than the second width, the fourth width is greater than the third width, and the fifth width is greater than the fourth width. In any of the embodiments, the crowns formed by the struts with the fifth width are disposed adjacent a minor axis of the frame and the crowns formed by the struts with the first width are disposed adjacent a major axis of the frame.

In any of the embodiments, when the frame is in the radially collapsed state, the plurality of crowns at at least one of the inflow end or the outflow end are non-planar, and when the frame is in the radially expanded state the plurality of crowns at the at least one of the inflow end or the outflow end are substantially planar.

In any of the embodiments, the plurality of struts at the inflow end and the plurality of struts at the outflow end may be of a non-uniform length.

In any of the embodiments, at least one of the inflow end or the outflow end comprises crowns of the plurality of crowns, and the plurality of struts forming the crowns at the outflow end or the inflow end each have a width selected from a group consisting of a first width, a second width, a third width, a fourth width, and a fifth width.

In any of the embodiments, the prosthetic valve may comprise four leaflets.

In any of the embodiments, the frame may be balloon expandable.

Embodiments hereof relate to a system for percutaneously delivering a heart valve prosthesis to a site of a native heart valve. The system includes a delivery catheter and a heart valve prosthesis in a radially collapsed configuration for delivery disposed at a distal portion of the delivery catheter. The heart valve prosthesis includes a radially expanded configuration wherein the heart valve prosthesis has a substantially elliptical shape, the substantially elliptical shape formed by varying a stiffness of at least one strut of a plurality of struts of a frame of the heart valve prosthesis.

In any of the embodiments, the stiffness of the at least one strut may be varied by changing a width of the at least one strut. In any of the embodiments, when the heart valve prosthesis is in the radially expanded configuration, at least one strut with a greatest width of the plurality of struts is disposed adjacent a minor axis of the heart valve prosthesis, and at least one strut with a smallest width of the plurality of struts is disposed adjacent a major axis of the heart valve prosthesis.

In any of the embodiments, the heart valve prosthesis may be balloon expandable, the delivery catheter may comprise a balloon at a distal portion thereof with an inflated state in which the balloon is substantially elliptically shaped in cross-section, and the heart valve prosthesis in the radially collapsed configuration may be disposed over the balloon in an uninflated state such that a major axis of the heart valve prosthesis is circumferentially aligned with a major axis of the balloon.

In any of the embodiments, the delivery catheter may further include a radiopaque marker coupled thereto and aligned with the major axis of the balloon.

Embodiments hereof also relate to method of deploying a substantially elliptically shaped heart valve prosthesis. The method includes loading a substantially elliptically shaped heart valve prosthesis in a radially collapsed configuration onto a delivery catheter, positioning the delivery catheter with the heart valve prosthesis at a native heart valve, aligning a major axis of the heart valve prosthesis with a major axis of an annulus of the native heart valve, and deploying the heart valve prosthesis at the annulus of the native heart valve.

In any of the embodiments, the heart valve prosthesis may be balloon expandable, and the step of loading the substantially elliptically shaped heart valve prosthesis onto the delivery catheter may comprise crimping the substantially elliptically shaped heart valve prosthesis onto an outer surface of a substantially elliptically shaped balloon in an uninflated state, wherein the major axis of the heart valve prosthesis is circumferentially aligned with a major axis of the balloon, and the step of deploying the heart valve prosthesis comprises transitioning the balloon from the uninflated state to an inflated state to transition the heart valve prosthesis from the radially collapsed configuration to the radially expanded configuration.

In any of the embodiments, the delivery catheter may include a radiopaque marker aligned with the major axis of the substantially elliptically shaped balloon and the major axis of the substantially elliptically shaped heart valve prosthesis, and the step of aligning the major axis of the heart valve prosthesis with the major axis of the annulus of the native heart valve comprises aligning the radiopaque marker with the major axis of the annulus of the native heart valve.

In any of the embodiments, the native heart valve may be a native aortic valve, a native mitral valve, a native pulmonic valve, or a native tricuspid valve.

In any of the embodiments, the native heart valve may be a prosthetic aortic valve, a prosthetic mitral valve, a prosthetic pulmonic valve, or a prosthetic tricuspid valve.

BRIEF DESCRIPTION OF DRAWINGS

FIG. 10 depicts a side view illustration of a distal portion of the system of FIG. 9.

FIG. 11 depicts a side view illustration of a distal portion of the system of FIG. 9 with the system rotated as compared to FIG. 10.

DETAILED DESCRIPTION OF THE INVENTION

Specific embodiments of the present invention are now described with reference to the figures, wherein like reference numbers indicate identical or functionally similar elements. The terms "distal" and "proximal", when used in the following description to refer to a delivery system or catheter are with respect to a position or direction relative to the treating clinician. Thus, "distal" and "distally" refer to positions distant from, or in a direction away from the treating clinician, and the terms "proximal" and "proximally" refer to positions near, or in a direction toward the clinician. The terms "distal" and "proximal", when used in the following description to refer to a device to be implanted into a vessel, such as a heart valve prosthesis, are used with reference to the direction of blood flow. Thus, "distal" and "distally" refer to positions in a downstream direction with respect to the direction of blood flow, and the terms "proximal" and "proximally" refer to positions in an upstream direction with respect to the direction of blood flow.

The following detailed description is merely exemplary in nature and is not intended to limit the invention or the application and uses of the invention. Although the description of the invention is in the context of an elliptically shaped heart valve prosthesis and systems and methods for deploying an elliptically shaped heart valve prosthesis at the site of a native heart valve, the invention may also be used in other body passageways where it is deemed useful. Furthermore, there is no intention to be bound by any expressed or implied theory presented in the preceding technical field, background, brief summary or the following detailed description.

The present invention in various embodiments relates to an elliptically shaped heart valve prosthesis for replacement of a native heart valve. FIGS. 1-7 illustrate an elliptically shaped heart valve prosthesis 100 according to an embodiment hereof. As described in more detail below, the heart valve prosthesis is substantially elliptical when viewed in cross-section. The heart valve prosthesis 100 includes a frame 102 supporting a prosthetic valve 104. The heart valve prosthesis 100 has a radially collapsed configuration for delivery, and a radially expanded configuration when deployed.

Figure 1:
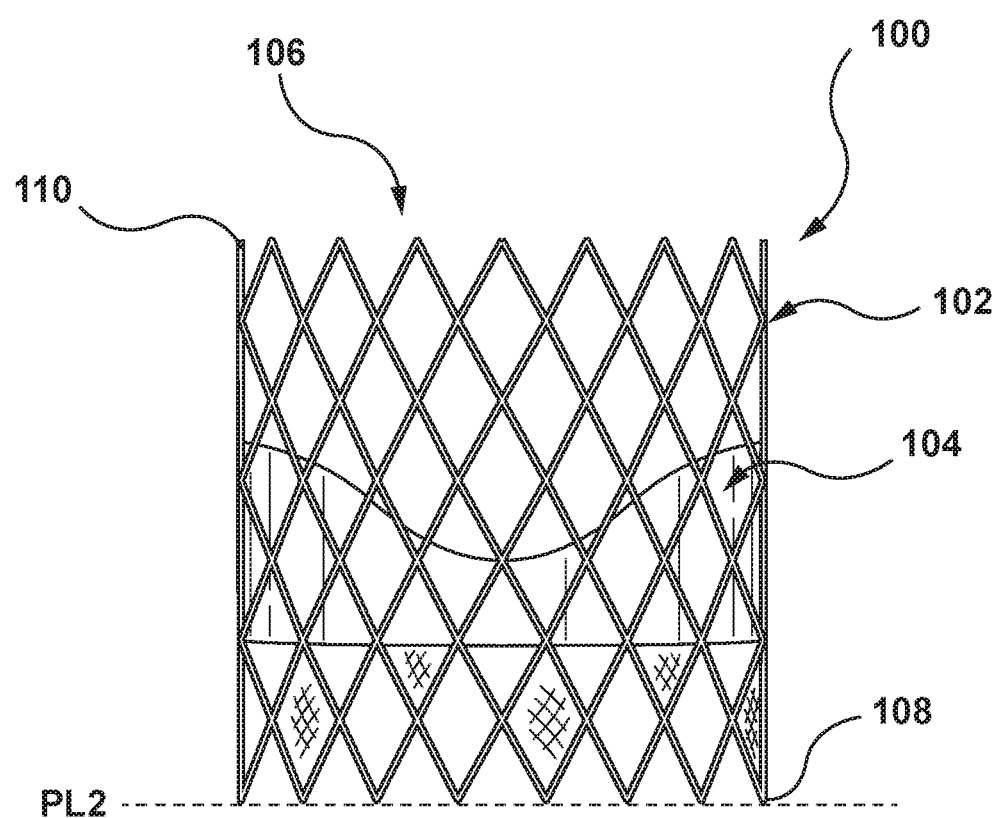
FIG. 1 depicts a schematic side view illustration of a heart valve prosthesis in accordance with an embodiment hereof, wherein the heart valve prosthesis is in a radially expanded configuration.
Figure 2:
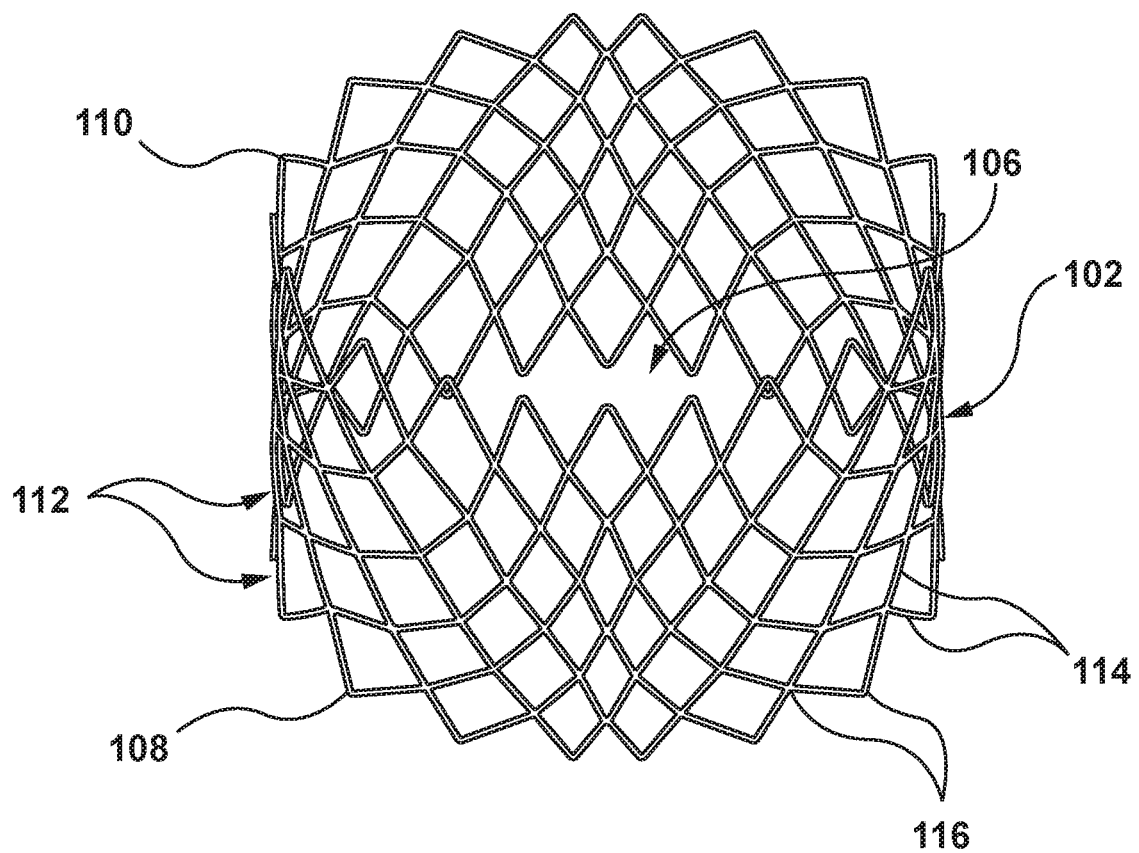
FIG. 2 depicts a perspective view illustration of a frame of the heart valve prosthesis of FIG. 1, wherein the frame is in a radially expanded configuration.

The frame 102, as shown in FIGS. 1 and 2, also referred to as a stent or support structure, is a structure including a lumen 106 extending from an inflow end 108 to an outflow end 110 of the frame 102. The frame 102 includes a radially collapsed state for delivery corresponding to the radially collapsed configuration of the heart valve prosthesis 100, and a radially expanded state when deployed corresponding to the radially expanded configuration of the heart valve prosthesis 100. The frame 102 is configured to engage tissue at an annulus of the native heart valve when the frame 102 is in the radially expanded state. The frame 102 is further configured to provide a secure mounting surface for the valve component 104. The frame 102 includes a plurality of struts 114 joined by bent segments or crowns 116 to form a plurality of bands 112. Each band 112 is coupled to an adjacent band 112 at the adjacent crowns 116 to form the frame 102. Although described as individual bands 112 connected together, this is not meant to be limiting, and the frame 102 may be formed as a unity, as by laser cutting a tube into the desired pattern.

Figure 3:
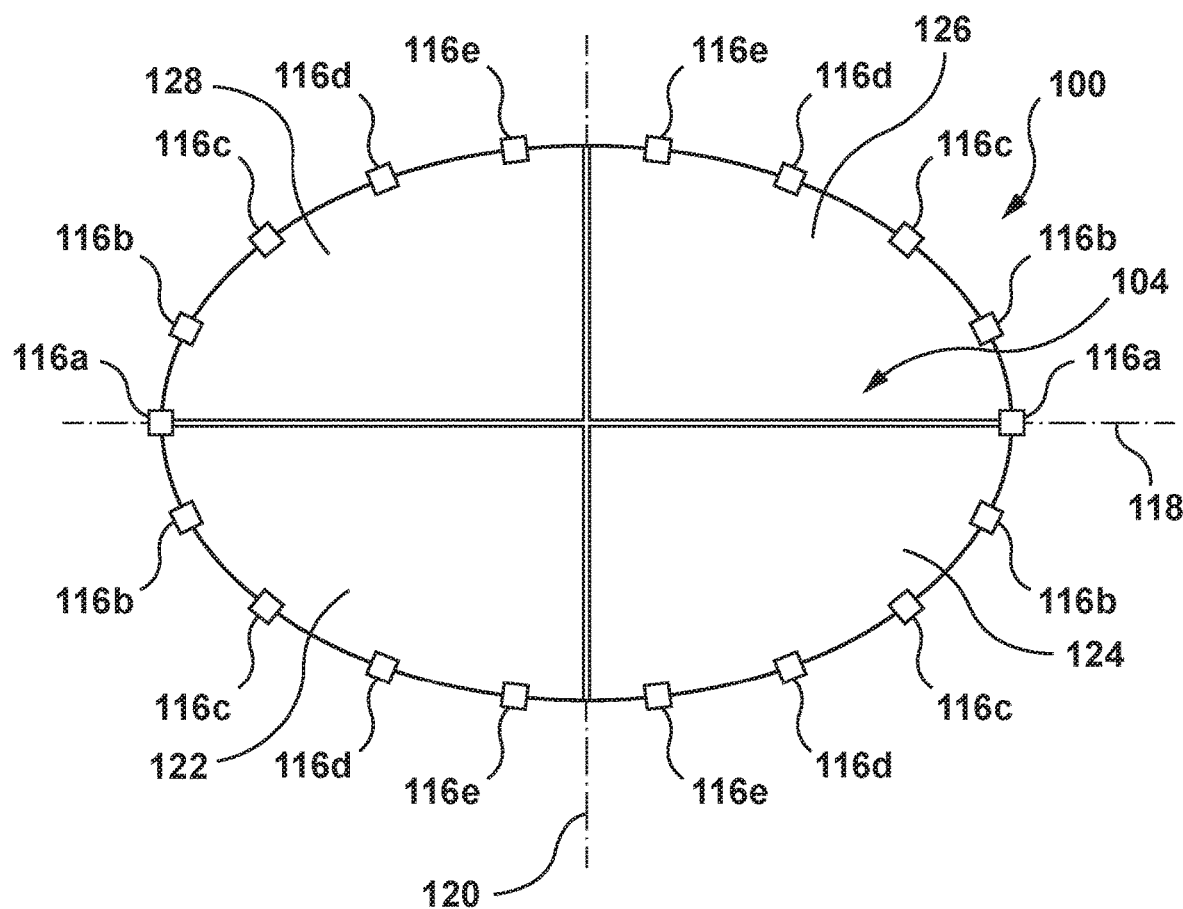
FIG. 3 depicts a top view illustration of the heart valve prosthesis of FIG. 1, wherein the heart valve prosthesis is in the radially expanded configuration.

Each strut 114 of the plurality of struts 114 includes a segment stiffness factor k, hereafter referred to as a "stiffness", as described below. The stiffness of each strut 114 of the plurality of struts 114 is varied such that when the frame 102 is in the radially expanded state, the frame 102 is substantially elliptically shaped when viewed in cross-section perpendicular to a central longitudinal axis LA of the frame 102. The substantially elliptical frame 102 includes a major axis 118 and a minor axis 120, with the major axis 118 being longer than the minor axis 120, as shown in FIG. 3. As used herein, the term "substantially elliptical" or "substantially elliptically shaped" means that the structure has an approximately elliptical shape with a major axis and a minor axis substantially perpendicular to the major axis, and that the major axis is greater in length than the minor axis. However, the shape need not be a mathematical ellipse such that oval shaped falls within the scope of "substantially elliptical" or "substantially elliptically shaped". The term "substantially perpendicular" as used herein with reference to the major axis and the minor axis of an ellipse or elliptical shape, means that the major axis and the minor axis intersect at approximately a 90° angle, plus or minus 10°.

Figure 4:
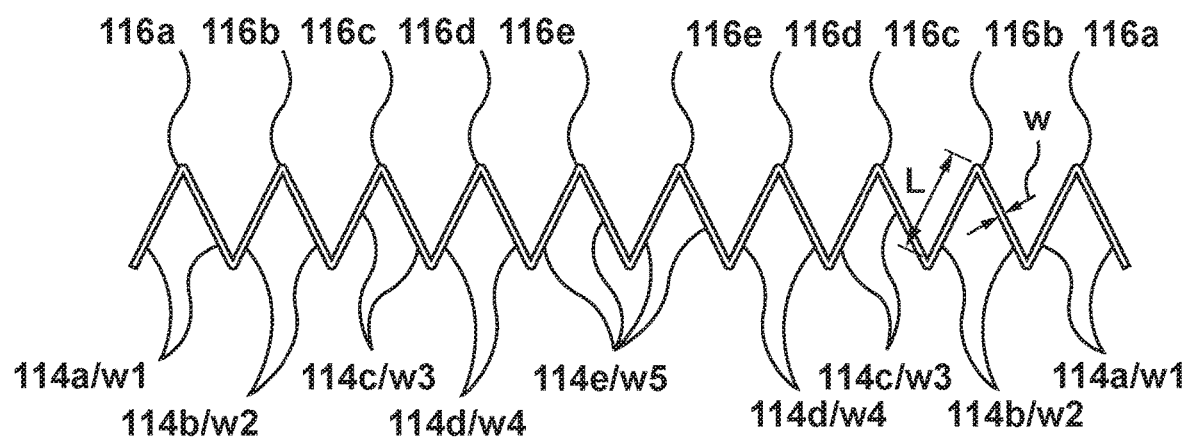
FIG. 4 depicts a partial side view illustration of a portion of the frame of the heart valve prosthesis of FIG. 1.

Each crown 116 is formed by a pair of struts 114, as best shown in FIG. 4. Each strut 114 includes the stiffness k, which is a measure of the rigidity of the strut 114, or, in other words, the measure of the ability or inability of the strut 114 to flex. The stiffness of each strut 114 may be expressed by the equation:

$$k = EtW^3/2L^3 \cos^2 \theta$$

In the equation, E is the elasticity modulus of a substance, t is the thickness of the wall of the segment or strut 114, W is the width of the segment or strut 114, L is the length of the segment or strut 114, and θ is the angle of deployment. The width W is measured from an outer surface of the strut 114 to the opposite outer surface of the strut 114 has shown in FIG. 4. With the elasticity modulus E, the wall thickness t, the length L, and the angle of deployment θ held constant for each strut 114, the stiffness k for each strut 114 may be varied by varying the width W of each strut 114. In embodiments hereof, the stiffness of the plurality of struts 114 is varied by varying a width W of at least one strut 114 of the plurality of struts 114. The greater the width W of the strut 114, the greater the stiffness k and the less flexible the strut 114. Thus, struts 114 with the greater width W are less flexible than struts 114 with a smaller width W, other factors being equal. As shown in FIGS. 3-4, varying the width W of the plurality of struts 114 at the inflow end 108 varies the stiffness k of the plurality of struts 114. Struts 114 with a greater width W and the corresponding greater stiffness k are less flexible and radially expand less than struts 114 with a smaller width W and a corresponding smaller stiffness k. The varying of the widths W of the plurality of struts 114 of the frame 102 permit the frame 102 to expand to an elliptical shape when expanded to the radially expanded state.

In the embodiment shown in FIGS. 1-7, the frame 102 includes eighteen (18) crowns 116 at the inflow end 108 and eighteen (18) crowns 116 at the outflow end 110. Further, as best shown in FIGS. 3-4, each strut 114 of the plurality of struts 114 is formed with one (1) of five (5) possible widths, a first width W1, a second width W2, a third width W3, a fifth width W4, or fifth width W5. In particular, FIG. 3 shows an embodiment wherein each crown 116 is either a first crown 116a, a second crown 116b, a third crown 166c, a fourth crown 116, or a fifth crown 116e. FIG. 4 shows that each first crown 116a is formed between two first struts 114a, each of which is the first width W1. Similarly, each second crown 116b is formed between two second struts 114b, each of which is the second width W2; each third crown 116c is formed between two third struts 114c, each of which is the third width W3; each fourth crown 116d is formed between two fourth struts 114d, each of which is the fourth width W4; and each fifth crown 116e is bounded by two fifth struts 114e, each of which is the fifth width W5. The first width W1 is smaller than the second width W2, which is smaller than the third width W3, which is smaller than the fourth width W4, which is smaller than the fifth width W5. In the embodiment of FIGS. 3-4, the inflow end 108 of the frame 102 includes two (2) first crowns 116a, four (4) second crowns 116b, four (4) third crowns 116c, four (4) fourth crowns 116d, and four (4) fifth crowns 116e.

The specific pattern or arrangement of the pairs of struts 114a-114e and corresponding crowns 116a-116e permit the frame 102 to expand to a predictable designed elliptical shape. When in the radially expanded state, the frame 102 includes a major axis 118 and a minor axis 120. The first struts 114a with the first widths W1 (smallest) are disposed adjacent ends of the major axis 118, and the fifth struts 114e with the fifth widths W5 (largest) are disposed adjacent ends the minor axis 120, as shown in FIG. 3. The difference in the width W of each strut 114, as well as the arrangement of the struts 114 may be selected to provide a specific ellipticity when the frame 102 is in the radially expanded state.

Figure 5:
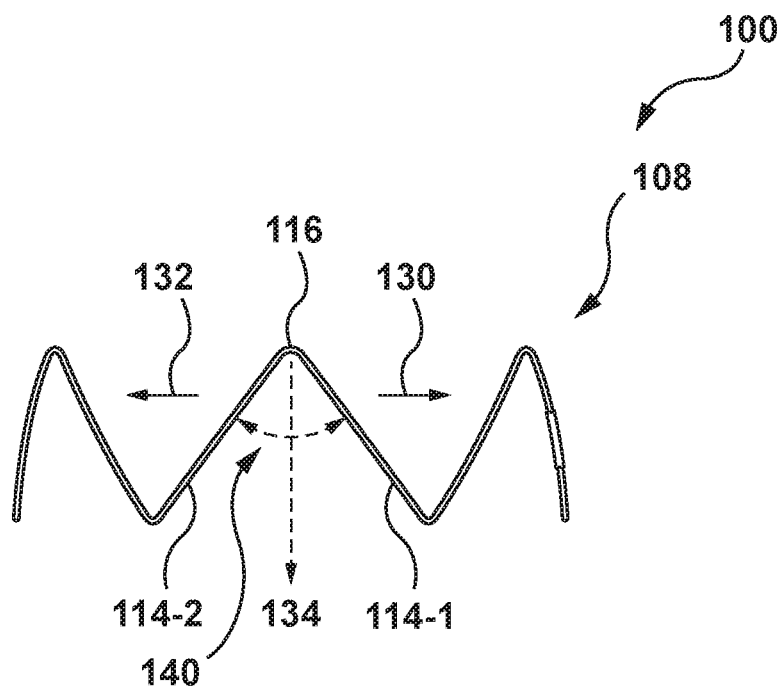
FIG. 5 depicts a partial side view illustration of an inflow end of the frame of the heart valve prosthesis of FIG. 1.

Referring next to FIG. 5, which depicts a partial side view of the inflow end 108 of the frame 102, each crown 116 includes an intrados 140. Each intrados 140 is the inner curve facing an acute angle I° of each crown 116. When the frame 102 is in the radially collapsed state, the intrados 140 of each crown 116 is substantially the same. As used herein, the terms "substantially" or "generally" mean approximately, with the intrados 140 of each crown 116 being equal within normal manufacturing tolerances. However, when the frame 102 is expanded, the struts 114 adjacent each crown 116 are moved in opposite directions (i.e., away from each other), as indicated by arrows 130, 132. The crown 116 is thus drawn axially towards a longitudinally middle portion of the frame, as indicated by the arrow 134, as shown in FIG. 5, thereby increasing the angle I°. The width W of each strut 114 adjacent the corresponding crown 116 determines the amount the angle I° of the intrados 140 increases and the axial distance in the direction of the arrow 134 the crown 116 moves during radial expansion of the frame 102.

Figure 6:
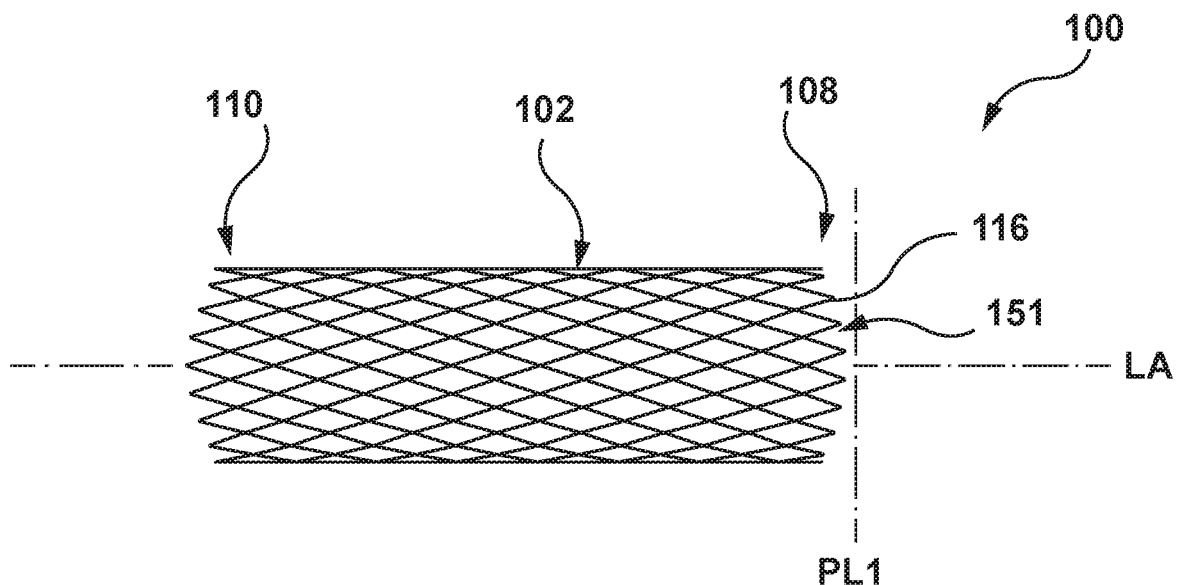
FIG. 6 depicts a side view illustration of the frame of the heart valve prosthesis of FIG. 1 with the frame in a radially collapsed configuration.
Figure 7:
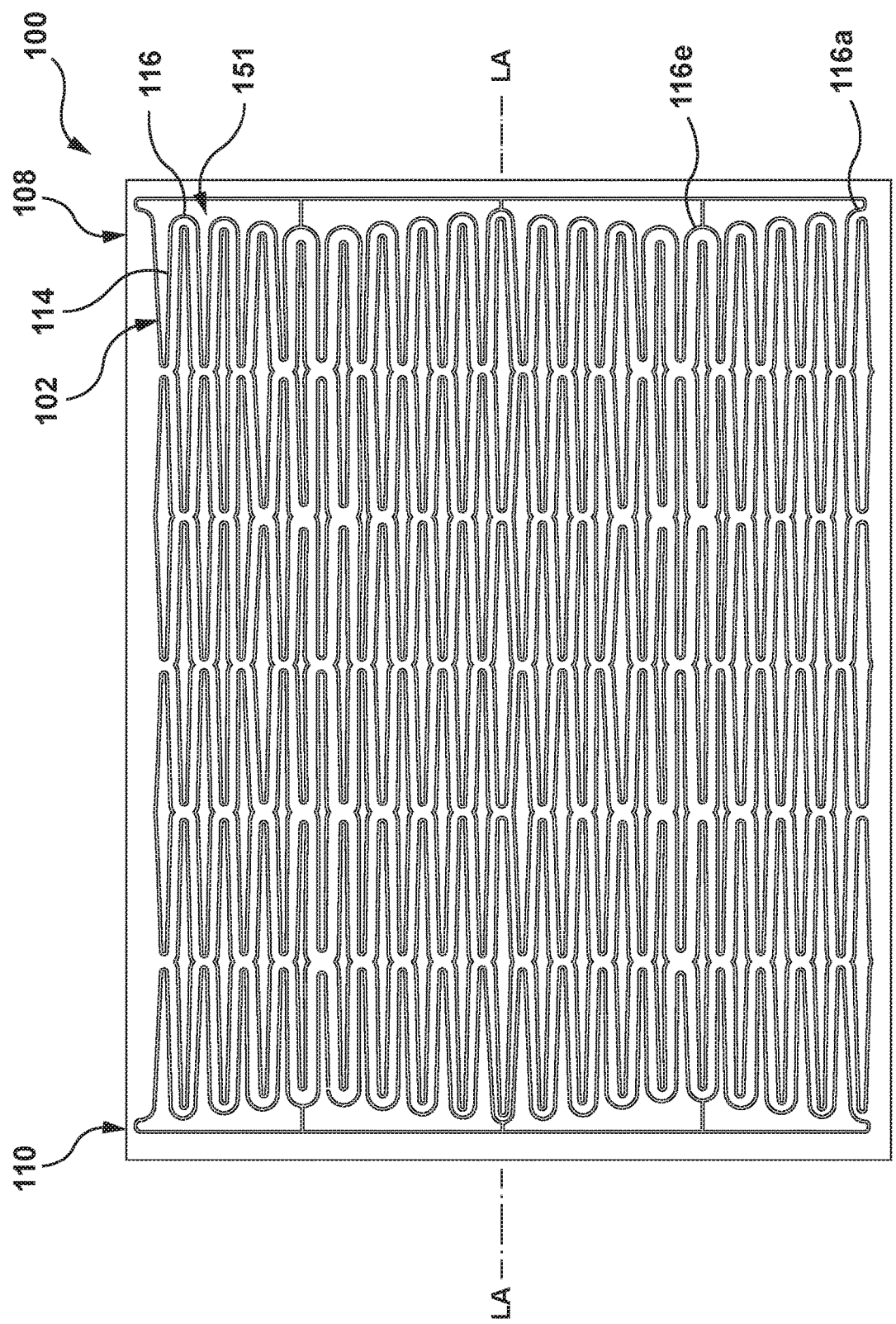
FIG. 7 depicts a side view illustration of the frame of heart valve prosthesis of FIG. 1 with the frame in a radially collapsed configuration and laid flat for illustrative purposes.

When the frame 102 is in the radially collapsed state, the plurality of crowns 116 at the inflow end 108 are non-planar, or not aligned in a first plane PL1, as shown in FIG. 6. In other words, the plurality of crowns 116 at the inflow end 108 are not aligned in a first plane PL1 perpendicular to a central longitudinal axis LA of the frame 102. Moreover, as best viewed in FIG. 7, the plurality of struts 114 at the inflow end 108 of the frame 102 are of a non-uniform length. More precisely, the crowns 116a formed of the struts 114a with the first width W1 have the greatest length L and extend axially the greatest distance from the inflow end 108 in the radially collapsed state. The greater the width W of each strut 114 of the corresponding crown 116, the shorter the length L of the strut 114 and the less the corresponding crown 116 extends from the end 108 when the frame 102 is in the radially collapsed state. During radial expansion of the frame 102, the first crowns 116a formed between the first struts 114a with the first widths W1 (smallest) move axially in the direction of the arrow 134 the largest distance, as compared to the other crowns 116. Moreover, the greater the width W of each strut 114 adjacent a corresponding crown 116, the less distance the corresponding crown 116 moves axially upon expansion. Thus, the crowns 116 at the inflow end 108 of the frame 102 move axially during radial expansion, such that when the frame 102 is in the radially expanded state, the plurality of crowns 116 at the inflow end 108 are substantially planar, or aligned in a second plane PL2, as shown in FIG. 1. While FIGS. 1-7 show and describe radial expansion at the inflow end 108 of the frame 102, this is by way of example and not limitation. It will be understood that the outflow end 110 of the frame 102 is configured similarly and descriptions of the movement of the crowns 116 and the corresponding intradoses 140 apply equally to the crowns 116 and the corresponding intradoses 140 at the outflow end 110.

While described herein with each strut 114 having one (1) of five (5) different strut widths W1-W5, this is by way of example and not limitation, and in other embodiments the frame 102 may include the plurality of struts 114 with each strut 114 including a width W from a group of more or fewer possible widths. Additionally, while the frame 102 has been described with eighteen (18) crowns 116 at each of the inflow end 108 and the outflow end 110, this too is by way of example and not limitation. In other embodiments, the frame 102 may include more or fewer crowns 116 at the inflow end 108 and the outflow end 110. Moreover, while the frame 102 shown in FIGS. 1-7 has a specific pattern of strut widths W around the frame 102 to elicit a specific ellipticity, the invention is not limited to the pattern shown. The width of each strut 114, as well as the distribution pattern of the plurality of struts 114 of varying widths W around the frame 102 may be altered to provide a desired ellipticity. For example, the ellipticity of the frame 102 of the heart valve prosthesis 100 may be in a range of 1.0 to 1.8.

In the embodiment of FIGS. 1-7 the heart valve prosthesis 100 is configured as a replacement for a native aortic valve. When configured as a replacement for a native aortic valve, the inflow end 108 of the frame 102 extends into and anchors within the aortic annulus of a patient's left ventricle and the outflow end 110 of the frame 102 is positioned in the patient's ascending aorta.

As described herein, the heart valve prosthesis 100 is expandable from the radially collapsed configuration to the radially expanded configuration. More precisely, the frame 102 is balloon expandable or mechanically expandable from the radially collapsed state to the radially expanded state. "Balloon expandable" or "mechanically expandable" as used herein means that a structure is plastically deformed such that the structure remains in the radially expanded state after being radially expanded by a suitable balloon or other mechanical expansion device. The frame 102 may be made from materials such as cobalt chromium alloys (e.g. MPN35, L605), platinum iridium, platinum chromium, or stainless steel alloys (e.g. 316L), and other suitable materials known to those skill in the art.

Alternatively, in another embodiment, a heart valve prosthesis may be self-expanding. "Self-expanding" as used herein means that a structure has a shape memory to return to the radially expanded configuration. Shape memory may be imparted on the structure that forms the frame using techniques understood in the art. In embodiments wherein the frame is self-expanding, the frame may be retained in a radially collapsed state for delivery by methods and devices understood by persons knowledgeable in the art. For example, and not by way of limitation, the self-expanding elliptical shaped heart valve prosthesis may be retained in the radially collapsed configuration by a suitable sheath or capsule or a cinching mechanism. Suitable cinching mechanisms and assemblies for retaining self-expanding heart valve prostheses are described in U.S. Pat. No. 9,629,718 to Gloss, which is incorporated herein by reference in its entirety. Suitable sheaths/capsules of a delivery catheter are described, for example, in in U.S. Pat. No. 8,926,692, to Dwork, which is incorporated herein by reference in its entirety.

As previously described herein, the valve prosthesis 100 includes the prosthetic valve 104 disposed within the lumen 106 of the frame 102. The prosthetic valve 104 may further include a skirt affixed to the frame 102. The prosthetic valve 104 is configured as a one-way valve to allow blood flow in one direction and prevent blood flow in the opposite direction. The prosthetic valve 104 blocks flow in one direction to regulate flow via valve leaflets. More particularly, and with reference back to FIG. 3, in an embodiment, the prosthetic valve 104 includes four (4) valve leaflets 122, 124, 126, 128. The valve leaflets 122, 124, 126, 128 form a replacement valve that opens due to a pressure differential such that pressure on the inflow side of the valve leaflets 122, 124, 126, 128 is greater pressure on the outflow side of the valve leaflets 122, 124, 126, 128. The prosthetic valve 104 closes when pressure on the outflow side of the valve leaflets 122, 124, 126, 128 is greater than on the inflow side. The valve leaflets 122, 124, 126, 128 may be sutured or otherwise securely and sealingly attached to an inner circumference of the frame 102, as understood by persons knowledgeable in the pertinent art.

The valve leaflets 122, 124, 126, 128 of the prosthetic valve 104 may be made of natural pericardial material obtained from, for example, heart valves, aortic roots, aortic walls, aortic leaflets, pericardial tissue, bypass grafts, blood vessels, intestinal submucosal tissue, umbilical tissue and the like from humans or animals, such as tissue from bovine, equine or porcine origins. Alternatively, the valve leaflets of the prosthetic valve 104 may be made of synthetic materials suitable for use as heart valve prosthesis leaflets in embodiments hereof including, but are not limited to polyester, polyurethane, cloth materials, nylon blends, and polymeric materials.

Figure 8:
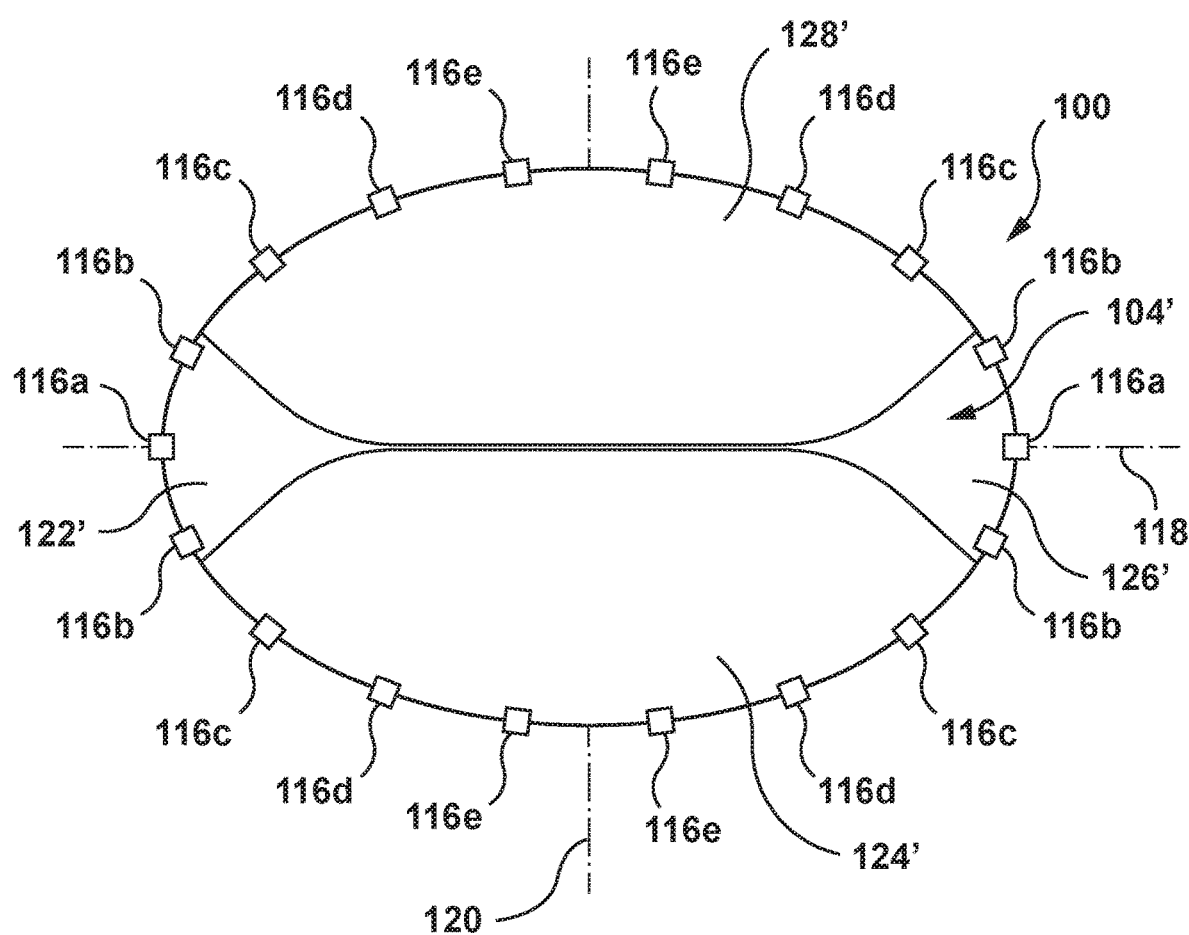
FIG. 8 depicts an end view illustration of the heart valve prosthesis of FIG. 1 with another embodiment of a leaflet configuration of a prosthetic valve of the heart valve prosthesis.

While the prosthetic valve 104 is shown with a specific pattern for the leaflets 122, 124, 126, 128, the invention is not limited to the pattern shown in FIG. 3. For example, and not by way of limitation, in an alternative embodiment a prosthetic valve 104' may include leaflets 122', 124', 126', 128' in a pattern as shown in FIG. 8.

The elliptical valve prosthesis 100 shown and described with respect to FIGS. 1-7 is shown as a one-piece valve prosthesis in that the frame 102 and prosthetic valve 102 are joined together as a single piece and delivered to the treatment site, and then deployed, as described in more detail below. However, the invention is not limited to such an embodiment. In other embodiments, an elliptical frame as described above may not include a prosthetic valve such that the elliptical frame is deployed to act as an anchor stent. A valve prosthesis as described above may then be delivered and deployed within the already-deployed anchor stent. The valve prosthesis in such an embodiment may or may not be elliptical, as described above. Due to the anchor stent already deployed within the annulus of the native heart valve, the frame of the valve prosthesis may have less outward radial force to maintain its location, because the frame is coupled to the anchor stent. Such an embodiment enables a smaller overall delivery profile because the frame of the valve prosthesis is not required to have as much radial force, and therefore may be thinner such that it can be crimped to a smaller diameter for delivery.

An embodiment of a system 301 for percutaneously delivering and deploying a heart valve prosthesis, such as the heart valve prosthesis 100 previously described herein, to a site of a native heart valve, is shown in FIGS. 9-12. The system 301 includes a delivery catheter 303 and the heart valve prosthesis 100. The delivery catheter 303 includes a handle 305, an outer shaft 307, an inner shaft 309, a distal tip 311, and a balloon 313.

The balloon 313 is coupled to a distal portion of the outer shaft 307 and distal portion of the inner shaft 309, as described in more detail below. The heart valve prosthesis 100, as previously described, may be crimped onto the balloon 313 in the radially collapsed configuration onto the balloon 313 for delivery to the native heart valve, and then may be deployed by inflating the balloon 313 to radially expand the valve prosthesis 100 to the radially expanded configuration. The balloon 313 may also be elliptical in cross-section to enable a smooth expansion of the elliptically shaped valve prosthesis 100. Thus, the major axis 118 of the heart valve prosthesis 100 is circumferentially or rotational aligned with a major axis 339 of the balloon 313, as shown in FIG. 12 and described below.

The handle 305 provides a surface for convenient handling and grasping by a user. While the handle 305 of FIG. 9 is shown with a generally cylindrical shape, this is by way of example and not limitation, and other shapes and sizes may be utilized.

Figure 9:
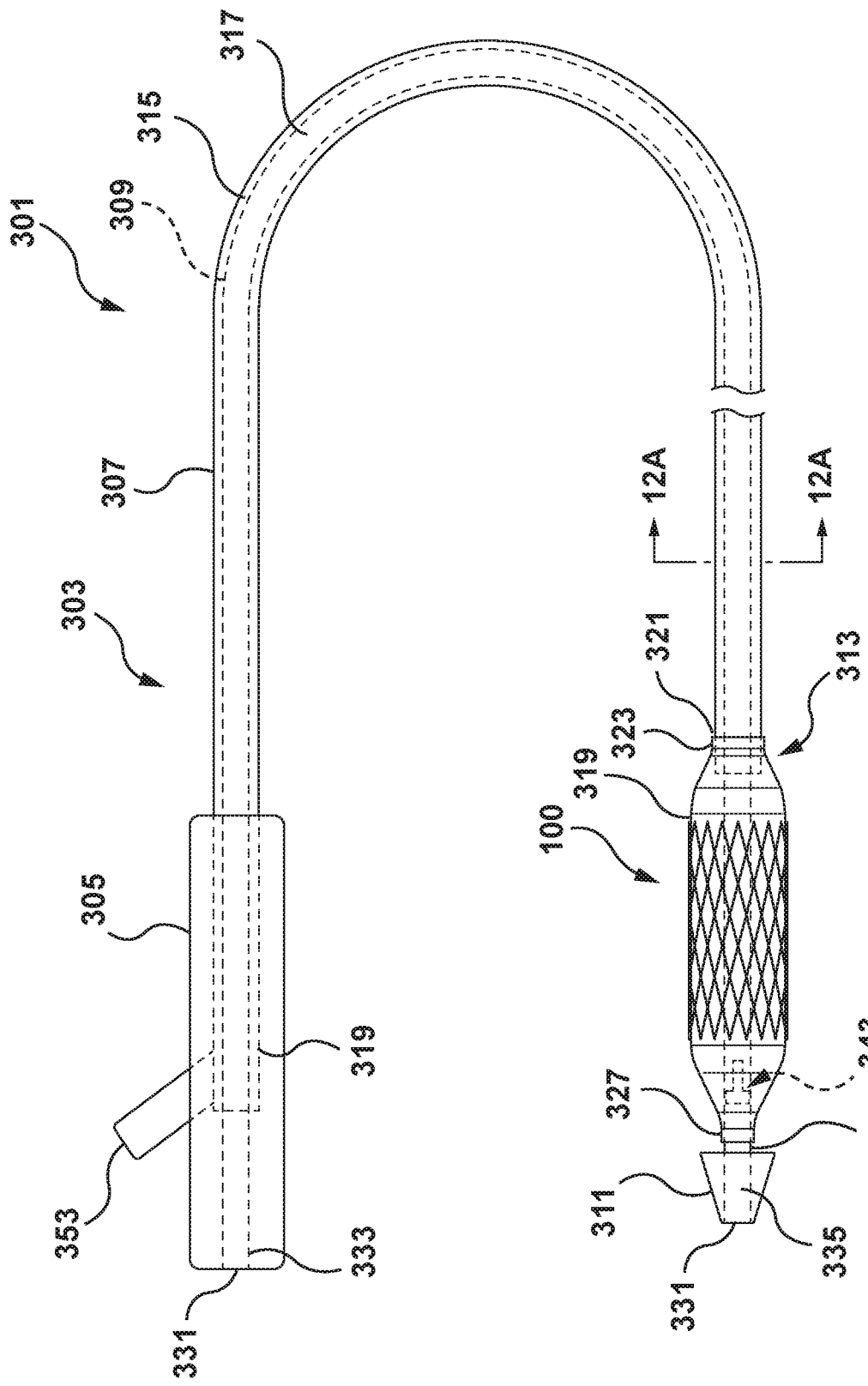
FIG. 9 depicts a side view illustration of a system for delivering, positioning, and deploying a substantially elliptical heart valve prosthesis.

Also shown in FIGS. 9-11, the inner shaft 309 includes a lumen 317 disposed therethrough. The lumen 317 is generally referred to as a guidewire lumen and enables a guidewire to be inserted into a distal port 329 of the lumen 317 such that the delivery catheter 303 may be tracked over the guidewire to the treatment site, as known to those skilled in the art. The inner shaft 309 includes a proximal end 332 couple to the handle 305 and including a proximal port 331 for a guidewire to extend through and into the lumen 317. The inner shaft also includes a distal end 325 coupled to the distal tip 311 and coupled to the balloon 313, as described in more detail below.

The outer shaft 307 of the delivery catheter 303 also includes a lumen 315 extending therethrough. The lumen 315 forms an annular inflation lumen between an outer surface of the inner shaft 309 and the inner surface of the outer shaft 307. At least a portion of the outer shaft 307 is configured for fixed connection to the handle 305. In an embodiment, a proximal end 319 of the outer shaft 307 may extend through and is coupled to the handle 305. As distal end 321 of the outer shaft is coupled to the balloon, as explained in more detail below.

Figure 12A:
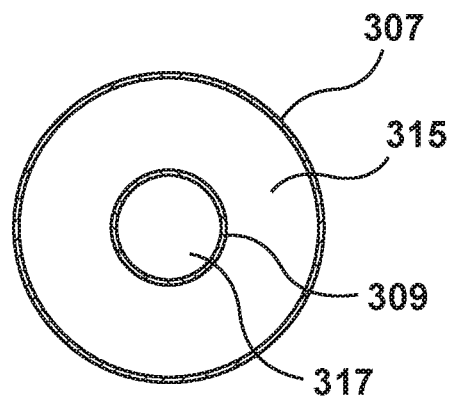
FIG. 12A depicts a cross-sectional illustration taken along line 12A-12A of FIG. 9.
Figure 12B:
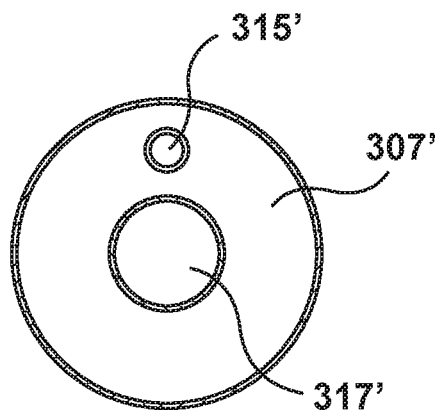
FIG. 12B depicts a cross-sectional view of an alternative embodiment of the delivery catheter of FIG. 9.
Figure 12C:
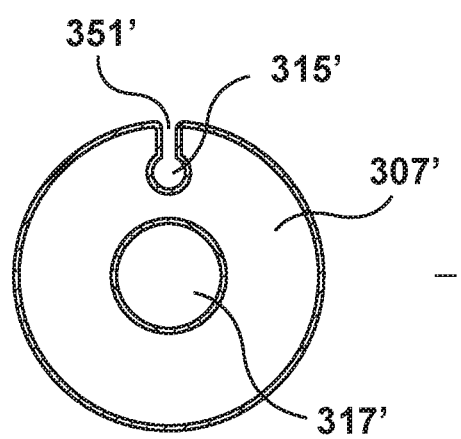
FIG. 12C depicts a cross-sectional view of the embodiment of FIG. 12B at a location within the balloon.

Although the outer shaft 307 and the inner shaft 309 are described herein as each being a single component, this is by way of example and not limitation, and the shafts 307, 309 may each include multiple components such as, but not limited to proximal and distal shafts or other components suitable for the purposes described herein. The outer and inner shafts 307, 309 may be formed of materials such as but not limited to polyurethane (e.g. Peliethane©, Elasthane™, Texin®, Tecothane®), polyamide polyether block copolymer (e.g. Pebax®, nylon 12), polyethylene, or other suitable materials Further, although the outer shaft 307 and the inner shaft 309 are described herein as two shafts in a co-axial arrangement, as shown in FIG. 12A, this is not meant to be limiting. For example, and not by way of limitation, there may be a single shaft 307' including both an inflation lumen 315' and a guidewire lumen 317', as known to those skilled in the art, and as shown in FIG. 12B.

As shown in FIGS. 9-11, a proximal neck 323 of the balloon 313 is attached to a distal end 321 the outer shaft 307. The outer shaft 307 terminates within an interior of the balloon 313 such that inflation fluid injected through the inflation lumen 315 exits the inflation lumen 315 within the interior of the balloon 313 to inflate the balloon 313. A distal neck 327 of the balloon 313 is attached to a distal end 325 of the inner shaft 309. The proximal and distal attachments of the balloon 313 to the outer and inner shafts 307, 309, respectively, may be via adhesives, fusion, mechanical attachment, or other methods known to those skilled in the art. Alternatively, in the embodiment shown in FIG. 12B, both the proximal neck 323 and the distal neck 327 of the balloon 313 are attached to the single shaft 307', and the inflation lumen 315' includes a port 351' exiting the shaft 307' between the proximal neck 323 and the distal neck 327 to inflate the balloon 313, as known to those skilled in the art, and shown in FIG. 12C.

As shown in FIGS. 9-11, the distal tip 311 includes a lumen 335 extending therethrough. The lumen 335 is sized to receive the distal end of the inner shaft 309 and provide a continuous lumen with lumen 317 of the inner shaft 309. The distal tip 311 may be coupled to the inner shaft 309 by methods such as, but not limited to adhesives, bonding, welding, fusing, mechanical connection, or other suitable coupling methods.

Figure 13:
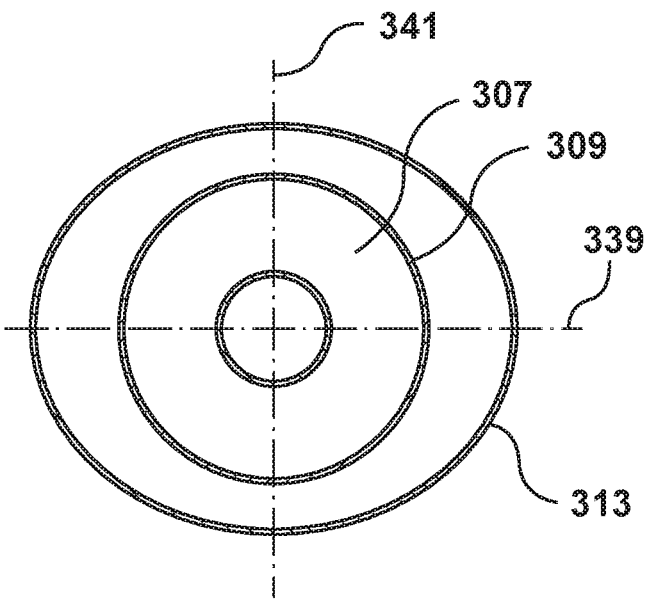
FIG. 13 depicts a cross-sectional view illustration of the balloon of the system of FIG. 9 with the balloon in an inflated state and the heart valve prosthesis removed for clarity.

When the interior of the balloon 313 is filled with an inflation fluid, the balloon 313 inflates to an inflated or radially expanded state. As shown in FIG. 13, the inflated balloon 313 is substantially elliptically shaped in cross-section transverse to the central longitudinal axis of the balloon 313. Thus, the inflated balloon 313, in cross-section, includes a major axis 339 and a minor axis 341, as shown in FIG. 13. The major axis 339 is longer than the minor axis 341. In FIG. 13, the heart valve prosthesis 100 has been omitted for clarity. The balloon 313 is configured to transition from the uninflated state to the inflated state to radially expand the heart valve prosthesis 100 from the radially compressed configuration to the elliptically shaped radially expanded configuration at the site of a native heart valve. Accordingly, the elliptical shape of the balloon 313 in the inflated state corresponds to the elliptical shape of the heart valve prosthesis 100 in the radially expanded configuration. While the balloon 313 is shown with a specific ellipticity, it will be understood that this is by way of example and not limitation, and that alternative ellipticities may be utilized. For example, the ellipticity of the balloon 313 may be in a range of 1.0 to 1.8. The balloon 313 may be a standard construction noncompliant or semi-compliant balloon constructed of materials such as, but not limited to polyethylene terephthalate (PET), nylon, or polyurethane.

In an embodiment, the delivery catheter 303 includes a radiopaque marker 343, as shown in FIG. 9-11. In the embodiment shown in FIGS. 9-11, the marker 343 is attached to or part of the inner shaft 309 adjacent the distal end 325 of the inner shaft 309. However, this is not meant to be limiting, and the marker 343 may be attached to or part of the outer shaft 307 adjacent the distal end thereof, or adjacent a distal end of the shaft 307' in the embodiment of FIGS. 12B-12C. In an embodiment, the marker 343 includes a head 345 and a tail 347 extending substantially perpendicular to the head 345. The tail 347 of the marker 343 is circumferentially aligned with one of the axes 339, 341 of the balloon 313. For example, the tail 347 may be circumferentially aligned with the major axis 339 of the balloon 313. Further, the heart valve prosthesis 100 is crimped onto the balloon 313 such that the major axis 118 of the frame 102 is aligned with the major axis 339 of the balloon 313, and hence is aligned with the tail 347 of the marker 343. Thus, when delivered to the treatment site, the treating clinician can align the tail 347 of the marker 343 with the larger axis of the annulus of the native heart valve such that the major axes 118, 339 of the heart valve prosthesis 100 and the balloon 313, respectively, are aligned with the larger axis of the annulus. As can be seen by comparing FIGS. 10 and 11, when viewing the delivery catheter 303, the treating clinician can determine if the major axes 118, 339 are in line with the view provided, as shown in FIG. 10, or are not aligned with the view, as shown in FIG. 11, which shows the major axes 118, 229 rotated by approximately 90 degrees.

The marker 343 may be formed of materials such as, but not limited to, platinum, gold, platinum iridium, or any other suitable material. The marker 343 may be coupled to the inner shaft 309, the outer shaft 307, or the shaft 307' by methods such as, but not limited to adhesives, bonding, welding, fusing, mechanical connection, or other suitable coupling methods, or may be formed as part of the shaft. The term "radiopaque" refers to the ability of a substance to absorb X-rays. Few substances will transmit 100% of X-rays and few substances will absorb 100% of X-rays. For the purposes of this disclosure, "radiopaque" will refer to those substances or materials which have suitable visibility for heart valve procedures when being imaged by an X-ray imaging device such as but not limited to a fluoroscope.

Although the marker 343 is shown with a head 345 and a tail 347, this is not meant to be limiting, and other designs may be used such that a treating clinician is able to align the marker with a larger or smaller axis of the annulus AN of the native heart valve AV, as explained in more detail below.

Figure 14:
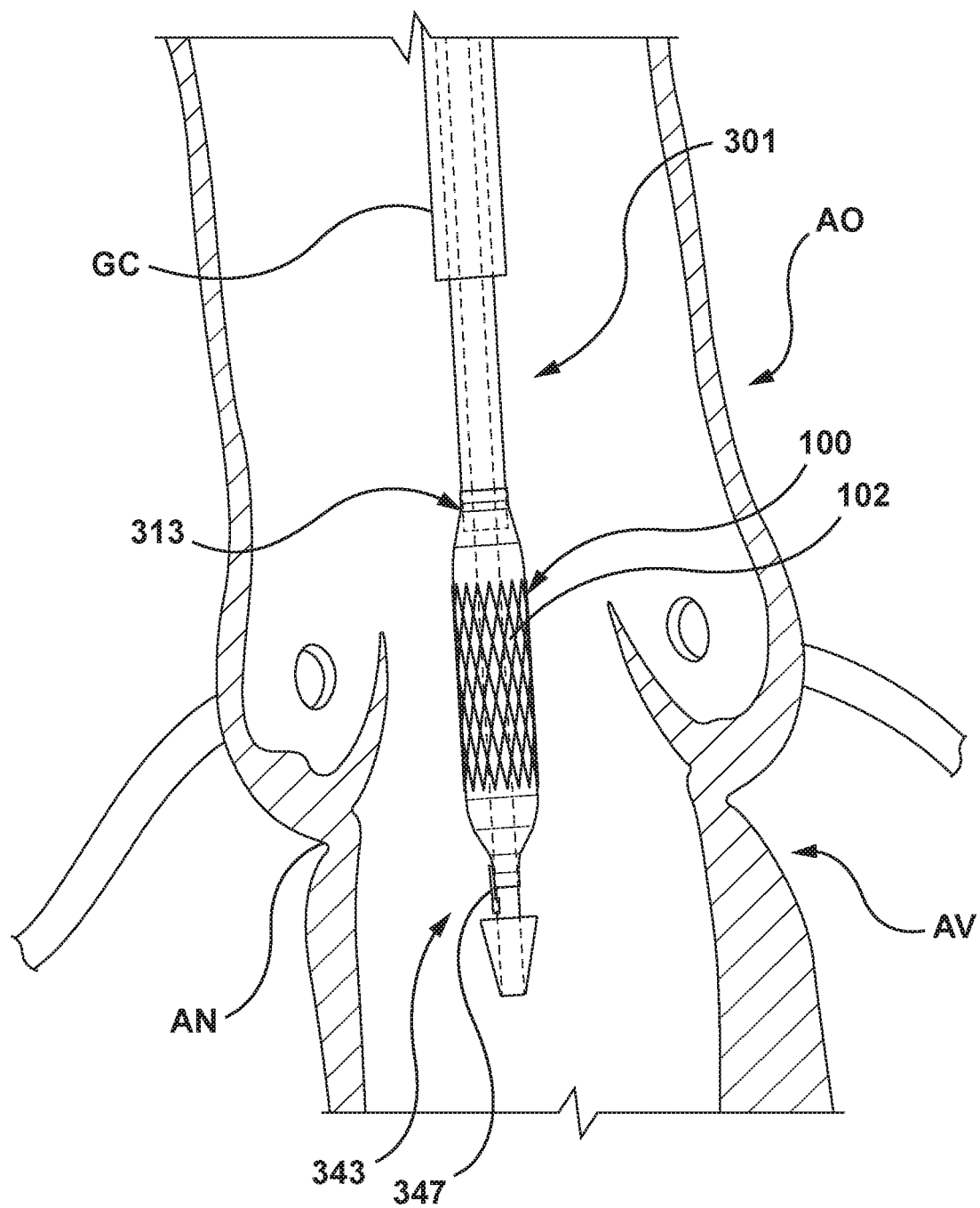
FIG. 14 depicts a cut away view illustration of a native heart with the system of FIG. 9 being delivered to the site of a native aortic valve.

FIGS. 14-17 are sectional cut-away views of a heart HE illustrating a method for delivery, positioning, and deploying the heart valve prosthesis 100 using the system 301 of FIG. 9 in accordance with an embodiment hereof. With reference to FIG. 14, the system 301 is shown having been introduced into the vasculature via a percutaneous entry point, e.g., via the Seldinger technique, and tracked through the vasculature and into the aorta AO until the heart valve prosthesis 100 is in proximity to and/or apposition with an annulus AN of the native aortic valve AV. Intravascular access to the aorta AO may be achieved via a percutaneous access site to femoral artery access up to the aorta AO, or other known access routes. Thereafter, a guidewire GW is advanced through the circulatory system, eventually arriving at the heart HE. Once the guidewire GW is positioned, a guide catheter GC is advanced through the vasculature and positioned proximate or downstream to the native aortic valve AV. The proximal end of the guidewire may then be loaded into the port 329 at the distal end of the delivery catheter 303, and the delivery catheter may be advanced to the treatment site over the guidewire. Although described herein as a transfemoral approach for percutaneously accessing the native aortic valve AV, the heart valve prosthesis 100 may be positioned within the desired area of the heart HE via other methods. In addition, although described with the use of the guide catheter GC and the guidewire GW, in another embodiment hereof the delivery catheter 303 may access the aorta AO without the use of the guidewire GW and/or the guide catheter GC.

With reference back to FIG. 14, it will be understood that the system 301 is assembled with the heart valve prosthesis 100 loaded onto the delivery catheter 303 with the heart valve prosthesis 100 in the radially collapsed configuration and disposed about the outer surface of the balloon 313 in the uninflated state, with the major axis 118 of the frame 102 of the heart valve prosthesis 100 circumferentially aligned with the tail 347 of the marker 343. With the system 301 so assembled, the system 301 is advanced to the site of the native aortic valve AV until the heart valve prosthesis 100 is positioned within the annulus AN of the native aortic valve AV.

As can be seen in FIG. 14, the marker 343 on the delivery catheter 303 is seen on the left side of the inner shaft 309.

Figure 15:
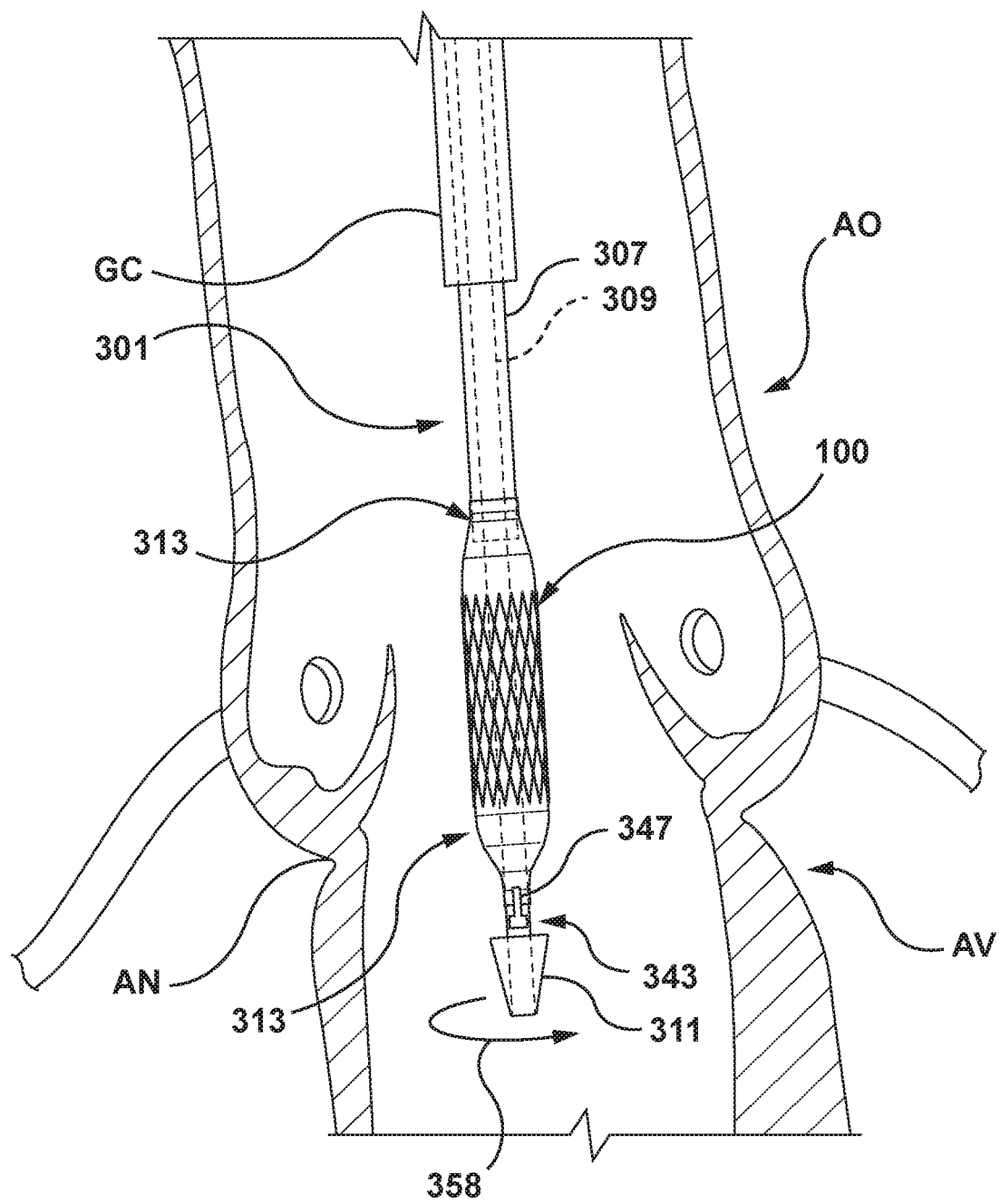
FIG. 15 depicts a cut away view illustration of a native heart with the system of FIG. 9 delivered to the site of a native aortic valve and rotated as compared to FIG. 14.

Thus, the major axes 118, 339 of the frame 102 and balloon 313, respectively, are rotated 90 degrees with respect to the view of FIG. 14. In other words, the major axes 118, 330 are aligned left-right in the view of FIG. 14. If the view of FIG. 14 is such that the major axis of the annulus AN of the native aortic valve is left-right, then no further action is necessary. If however, the larger axis of the annulus AN is front-back in the view of FIG. 14, then the major axes 118, 339 of the frame 102 and balloon 303 are not aligned with the major axis of the annulus AN. In such a situation, as shown in FIG. 15, the handle 305 (not visible in FIGS. 14-17) may be rotated (in this example, counter-clockwise in a direction of the arrow 358) to align the tail 347 of the marker 343 with the major axis of the annulus AN of the native aortic valve AV. Radial alignment of the major axis 118 of the frame 102 of the heart valve prosthesis 100 and the major axis of the annulus AN of the heart HE insures optimal sealing of the elliptically shaped heart valve prosthesis 100 with the elliptically shaped annulus AN to prevent paravalvular leakage (PVL) when the heart valve prosthesis 100 is deployed therein. Those skilled in the art would understand that instead of the tail 347 of the marker 343 being aligned with the major axes 118, 339 of the frame 102 and the balloon 339, in other embodiments, the tail 347 of the marker 343 may be aligned with the minor axes 120, 341 of the frame 102 and the balloon 339 such that the treating clinician may align the tail 347 with the minor axis of the annulus AN. Depending on the view of the fluoroscope used, it may be desirable such that when the delivery catheter 303 is properly aligned, the tail 347 is visible at the "front" of the catheter 303, in FIG. 15.

Figure 16:
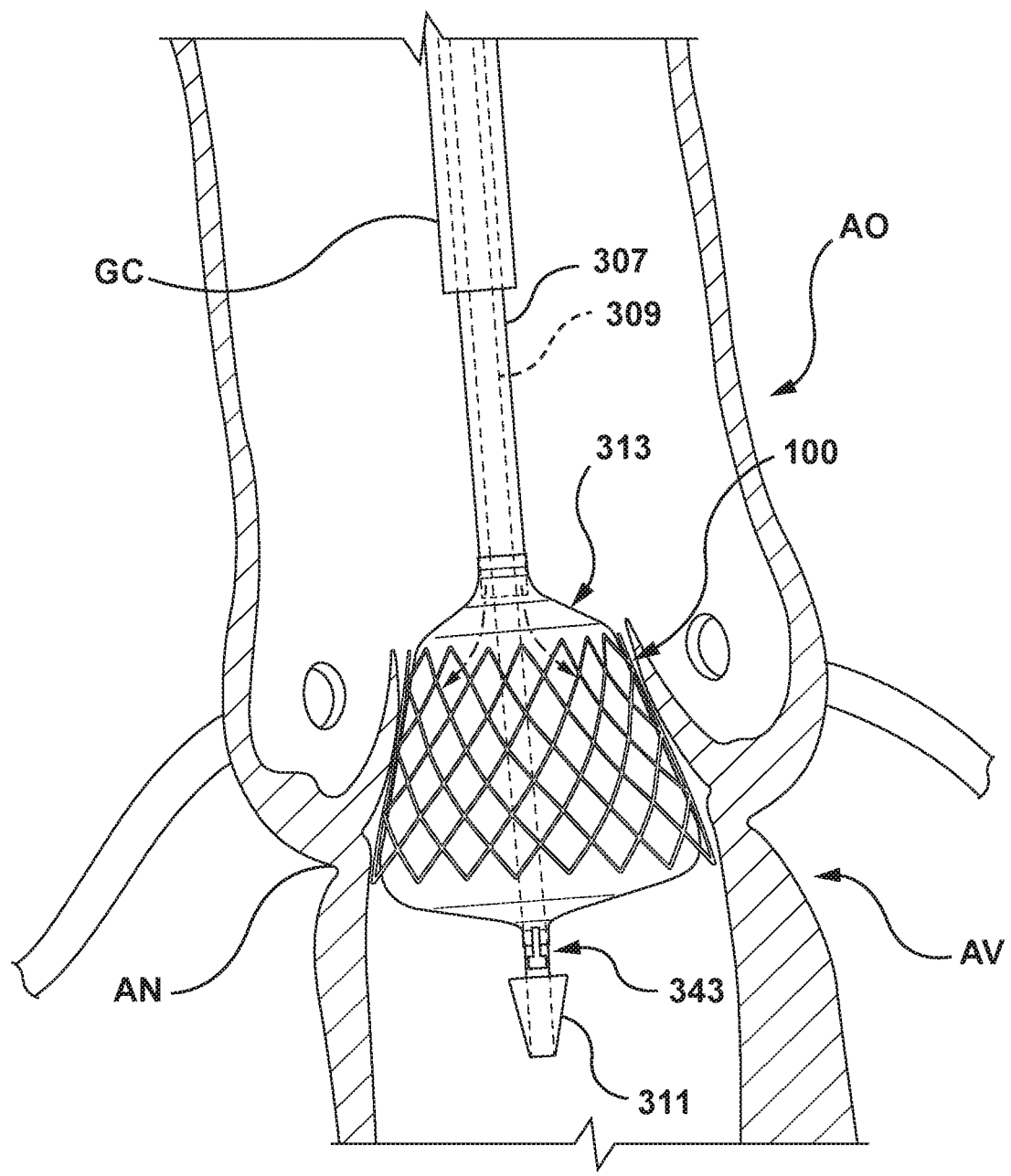
FIG. 16 depicts a cut away view illustration of a native heart with the balloon of the system of FIG. 9 being inflated to radially expand the heart valve prosthesis.

When the heart valve prosthesis 100 is properly aligned with and positioned within the annulus AN of the native aortic valve AV, and the clinician is ready to deploy the heart valve prosthesis 100, inflation fluid under pressure is pumped into the inflation lumen 315 through an inflation port 353 (FIG. 9) such that the inflation fluid exits a distal opening of the outer shaft 307 and the balloon 313 to inflate the balloon 313, as shown in FIG. 16. As the balloon 313 transitions from the uninflated state to the inflated state, the balloon 313 radially expands the heart valve prosthesis 100 disposed thereon from the radially collapsed configuration to the elliptically shaped radially expanded configuration. The heart valve prosthesis 100 plastically deforms to the radially expanded configuration and engages the tissue at the annulus AN of the native aortic valve AV. Alignment of the major axis 339 of the balloon 313 and the co-aligned major axis 118 of the frame 102 of the heart valve prosthesis 100 with the major axis of the annulus AN of the native aortic valve AV in the previous step insures that the heart valve prosthesis 100 fully expands and sealingly conforms to the substantially elliptical shape of the annulus AN of the native aortic valve AV.

Figure 17:
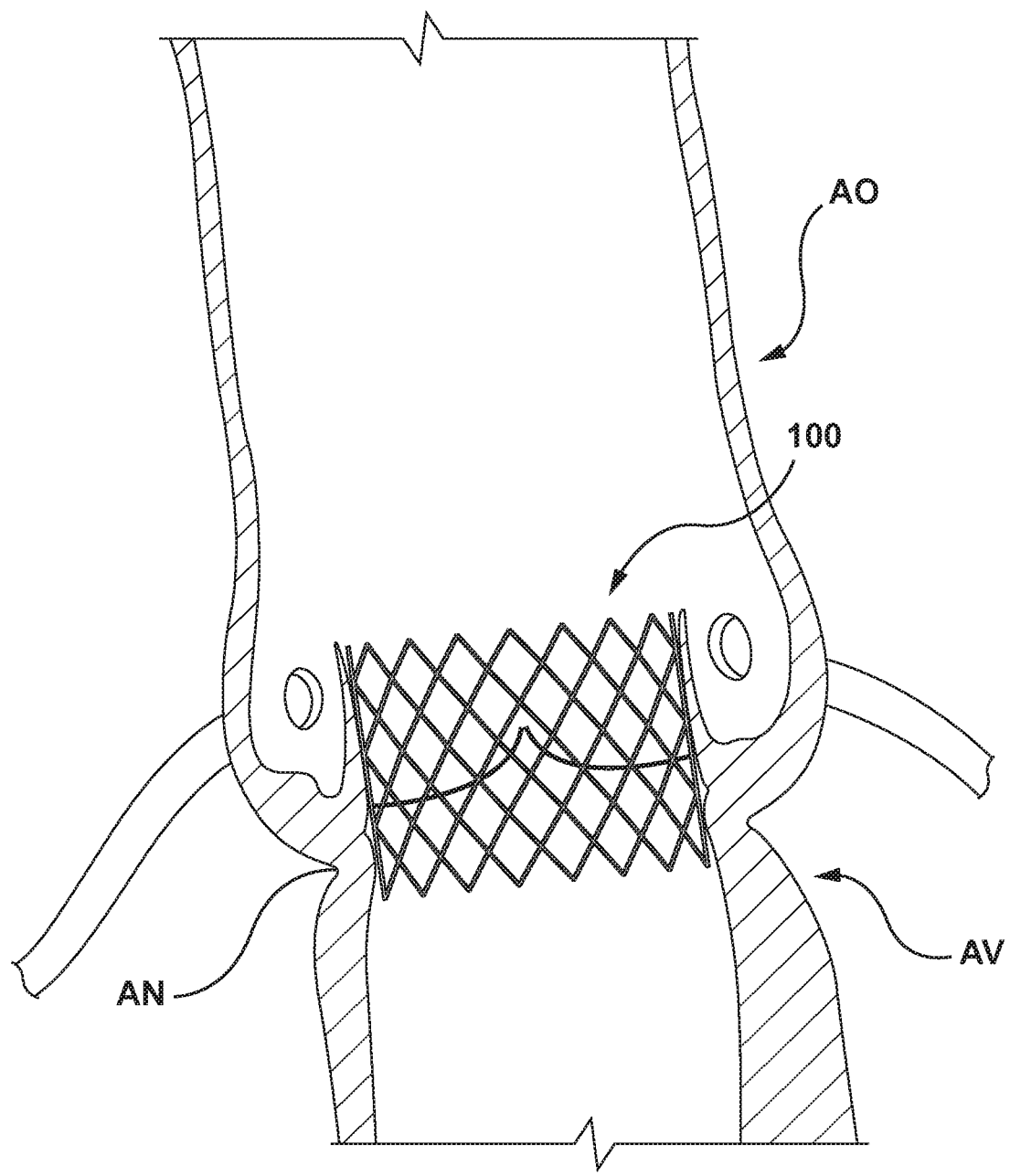
FIG. 17 depicts a cut away view illustration of the heart with the delivery catheter of the system of FIG. 9 removed after the heart valve prosthesis has been radially expanded at the site of the native aortic valve.

Following the successful positioning and deployment of the heart valve prosthesis 100 within the annulus AN of the native aortic valve AV, pressure on the inflation fluid is released and the inflation fluid flows out of the balloon 313 and through the inflation lumen 315 such that the balloon 313 transitions from the inflated state to the uninflated state. Once the balloon 313 is in the uninflated state, the delivery catheter 303, the guide catheter GC, and the guidewire GW can be removed using established procedures. With the delivery catheter 303 removed, the heart valve prosthesis 100 remains at the annulus AN of the native aortic valve AV, as shown in FIG. 17.

Imaged guidance, e.g., intracardiac echocardiography (ICE), fluoroscopy, computed tomography (CT), intravascular ultrasound (IVUS), optical coherence tomography (OCT), or other suitable guidance modality, or combination thereof, may be used to aid the clinician's delivery positioning, and radial alignment of the heart valve prosthesis 100.

While the method of FIGS. 14-17 is described with the heart valve prosthesis 100 of FIGS. 1-7 and the system 301 of FIGS. 9-13, this is not meant to be limiting. It will be understood that other embodiments of substantially elliptically shaped heart valve prostheses may be utilized with a similar method.

Although the method has been described with respect to the delivery, positioning, radial alignment, and deployment of a heart valve prosthesis at the site of a native aortic valve, the method may be utilized at other locations.

While only some embodiments according to the present invention have been described herein, it should be understood that they have been presented by way of illustration and example only, and not limitation. Various changes in form and detail can be made therein without departing from the spirit and scope of the invention. Further, each feature of each embodiment discussed herein, and of each reference cited herein, can be used in combination with the features of any other embodiment. All patents and publications discussed herein are incorporated by reference herein in their entirety.

What is claimed is:

1. A heart valve prosthesis comprising:
a frame including a lumen, the frame including a plurality of bands extending circumferentially around a central longitudinal axis of the frame and comprising a plurality of struts and a plurality of crowns, an inflow end, and an outflow end opposite the inflow end, wherein the frame is configured to assume a radially collapsed state and a radially expanded state; and
a prosthetic valve disposed within the lumen of the frame, wherein stiffness of the plurality of struts in a band of the plurality of bands is varied around a circumference of the frame such that when the frame is in the radially expanded state, the frame is substantially elliptically shaped in cross-section transverse to the central longitudinal axis,
wherein the stiffness of the plurality of struts is varied by varying respective widths of the plurality of struts, wherein the width of each strut of the plurality of struts in the band of variable stiffness of the frame is selected from a group consisting of a first strut width, a second strut width, a third strut width, a fourth strut width, and a fifth strut width, wherein the band of variable stiffness includes at least one strut from each of the first width, the second width, the third width, the fourth width, and the fifth width.

2. The heart valve prosthesis of claim 1, wherein when the frame is in the radially expanded state, at least one strut in the band of variable stiffness with a greatest width of the plurality of struts is disposed adjacent a minor axis of the frame in the cross-section, and at least one strut in the band of variable stiffness with a smallest width of the plurality of struts is disposed adjacent a major axis of the frame in the cross-section, wherein the major axis and the minor axis are substantially perpendicular to each other and to the central longitudinal axis.

3. The heart valve prosthesis of claim 1, wherein the band of variable stiffness is adjacent the inflow end or the outflow end of the frame and comprises eighteen crowns joining adjacent struts of the plurality of struts.

4. The heart valve prosthesis of claim 3,
wherein each of the eighteen crowns join two struts such that the plurality of struts consists of thirty-six struts including four struts of the first width, eight struts of the second width, eight struts of the third width, eight struts of the fourth width, and eight struts of the fifth width, wherein the second width is greater than the first width, the third width is greater than the second width, the fourth width is greater than the third width, and the fifth width is greater than the fourth width, and
wherein the varied widths of the struts varies the stiffness of the struts of the band of variable stiffness.

5. The heart valve prosthesis of claim 4, wherein the crowns joining the struts with the fifth width are disposed adjacent a minor axis of the frame and the crowns joining the struts with the first width are disposed adjacent a major axis of the frame.

6. The heart valve prosthesis of claim 1, wherein when the frame is in the radially collapsed state, the plurality of crowns at the inflow end or the outflow end of the frame are non-planar, and when the frame is in the radially expanded state the plurality of crowns at the inflow end or the outflow end of the frame are substantially planar.

7. The heart valve prosthesis of claim 1, wherein the plurality of struts at the inflow end and the plurality of struts at the outflow end are of a non-uniform length.

8. The heart valve prosthesis of claim 1, wherein the band of variable stiffness is at the inflow end or the outflow end of the frame.

9. The heart valve prosthesis of claim 1, wherein the prosthetic valve comprises four leaflets.

10. The heart valve prosthesis of claim 1, wherein the frame is balloon expandable.

11. A heart valve prosthesis comprising:
a frame including a lumen, the frame including a plurality of bands extending circumferentially around a central longitudinal axis of the frame and comprising a plurality of struts and a plurality of crowns, an inflow end, and an outflow end opposite the inflow end, wherein the frame is configured to assume a radially collapsed state and a radially expanded state; and
a prosthetic valve disposed within the lumen of the frame,
wherein stiffness of the plurality of struts in a band of the plurality of bands is varied around a circumference of the frame such that when the frame is in the radially expanded state, the frame is non-circular in shape in cross-section transverse to the central longitudinal axis,
wherein the stiffness of the plurality of struts is varied such that the stiffness increases from a first stiffness adjacent each end of a major axis of the frame in the cross-section to a second stiffness adjacent each end of a minor axis of the frame in the cross-section with at least a third stiffness between each end of the major axis and each end of the minor axis, wherein the second stiffness is greater than the first stiffness and the third stiffness is between the first stiffness and the second stiffness.

12. A system for percutaneously delivering a heart valve prosthesis to a site of a native heart valve, the system comprising:
a delivery catheter; and
a heart valve prosthesis configured to assume a radially collapsed configuration for delivery and a radially expanded configuration when deployed, the heart valve prosthesis including a frame and a prosthetic valve coupled to the frame, the frame having a plurality of circumferential bands each comprising a plurality of struts and a plurality of crowns, wherein the heart valve prosthesis is disposed in the radially collapsed configuration at a distal portion of the delivery catheter for delivery to a site of a native heart valve,
wherein when the heart valve prosthesis is in the radially expanded configuration, the heart valve prosthesis has a substantially elliptical shape in a cross-section lateral to a central longitudinal axis of the frame, the substantially elliptical shape formed by varying stiffness of the plurality of struts of at least one of the bands of the plurality of circumferential bands of the frame of the heart valve prosthesis,
wherein the stiffness of the plurality of struts is varied such that the stiffness increases from a first stiffness adjacent each end of a major axis of the frame in the cross-section to a second stiffness adjacent each end of a minor axis of the frame in the cross-section with at least a third stiffness between each end of the major axis and each end of the minor axis, wherein the second stiffness is greater than the first stiffness and the third stiffness is between the first stiffness and the second stiffness.

13. The system of claim 12, wherein the stiffness of the plurality of struts is varied by varying respective widths of the plurality of struts, and wherein when the heart valve prosthesis is in the radially expanded configuration, at least one strut with a greatest width of the plurality of struts is disposed adjacent the minor axis of the frame in the cross-section, and at least one strut with a smallest width of the plurality of struts is disposed adjacent the major axis of the frame in the cross-section, wherein the major axis and the minor axis are substantially perpendicular to each other and to the central longitudinal axis.

14. The system of claim 12, wherein
the heart valve prosthesis is balloon expandable,
the delivery catheter further comprises a balloon at the distal portion thereof,
the balloon is configured to assume an inflated state in which the balloon is substantially elliptically shaped in cross-section, and
the heart valve prosthesis in the radially collapsed configuration is disposed over the balloon in an uninflated state such that the major axis of the frame is circumferentially aligned with a major axis of the balloon.

15. The system of claim 14, wherein the delivery catheter further includes a radiopaque marker coupled thereto and aligned with the major axis of the balloon.

16. The system of claim 12, wherein the at least one band of variables stiffness of the frame is adjacent an inflow end or an outflow end of the frame, and wherein the at least one band of variable stiffness comprises eighteen crowns joining adjacent struts of the plurality of struts.

17. The system of claim 16, wherein the plurality of struts joined by the eighteen crowns each have a width selected from a group consisting of a first width, a second width, a third width, a fourth width, and a fifth width, and wherein the band includes at least one strut from each of the first width, the second width, the third width, the fourth width, and the fifth width.

18. The system of claim 17, wherein the plurality of struts joined by the eighteen crowns comprises thirty-six struts, wherein the thirty-six struts include four struts of the first width, eight struts of the second width, eight struts of the third width, eight struts of the fourth width, and eight struts of the fifth width, wherein the second width is greater than the first width, the third width is greater than the second width, the fourth width is greater than the third width, and the fifth width is greater than the fourth width, and wherein the varied widths of the struts of the at least one band of variable stiffness varies the stiffness of the struts of the at least one band of variable stiffness.

\* \* \* \* \*